United States Patent [19]

Krupa et al.

[11] Patent Number: 5,642,190
[45] Date of Patent: Jun. 24, 1997

[54] DUAL-AXIS PLASMA IMAGING SYSTEM FOR USE IN SPECTROSCOPIC ANALYSIS

[75] Inventors: Robert J. Krupa, Leominster, Mass.; Edward E. Owen, Nashua, N.H.

[73] Assignee: Thermo Jarrell Ash Corp., Franklin, Mass.

[21] Appl. No.: 522,755

[22] Filed: Sep. 1, 1995

[51] Int. Cl.$^6$ ................................................. G01J 3/30
[52] U.S. Cl. .......................... 356/316; 356/319; 356/326
[58] Field of Search ................................. 356/316, 318, 356/323, 325, 326, 328, 319

[56] References Cited

U.S. PATENT DOCUMENTS

| | | |
|---|---|---|
| 3,424,533 | 1/1969 | Hughes et al. |
| 3,692,415 | 9/1972 | Shiller |
| 3,879,126 | 4/1975 | Delew |
| 4,182,574 | 1/1980 | Quillfeldt |
| 4,234,252 | 11/1980 | Böttger et al. |
| 4,261,638 | 4/1981 | Wagner |
| 4,293,220 | 10/1981 | Denton et al. |
| 4,300,834 | 11/1981 | Demers et al. |
| 4,326,802 | 4/1982 | Smith, Jr. et al. |
| 4,394,091 | 7/1983 | Russo |
| 4,545,680 | 10/1985 | Smith, Jr. |
| 4,622,468 | 11/1986 | Stefanski et al. |
| 4,766,287 | 8/1988 | Morrisroe et al. |
| 4,820,048 | 4/1989 | Barnard |
| 5,005,934 | 4/1991 | Curtiss |
| 5,062,708 | 11/1991 | Liang et al. |
| 5,343,289 | 8/1994 | Crawford et al. |
| 5,483,337 | 1/1996 | Barnard et al. |

FOREIGN PATENT DOCUMENTS

| | | |
|---|---|---|
| 0019844 | 2/1987 | Japan |
| 0063841 | 3/1987 | Japan |
| 402201141 | 8/1990 | Japan |
| 1368810 | 10/1972 | United Kingdom |

OTHER PUBLICATIONS

Abstract of paper presented by Perkin Elmer Corporation, Abstract No. 576, FACSS XXII Meeting, Oct. 15–20, 1995.
Advertisement of Leeman Labs, Inc., (SAS) New England Section Newsletter, vol. 1, No. 2, Oct., 1995.

*Primary Examiner*—K. Hantis
*Attorney, Agent, or Firm*—Hopgood, Calimafde, Kalil & Judlowe

[57] ABSTRACT

A dual-axis plasma imaging system for use in spectroscopic analysis of material. The system includes a plasma torch having a tubular member with an upstream inlet end for receiving a flow of material to be analyzed and a downstream end for discharge of the material. An induction coil is provided for effecting plasma optical emission from the material, and a spectrometer for analyzing the emission. A first optical imaging device collects and focuses an axial emission component onto a primary aperture of the spectrometer. The first device is in a principal optical path between the tubular member and the spectrometer. A second optical imaging device in a secondary optical path collects and focuses a radial emission component onto the primary aperture of the spectrometer. The secondary path is angularly offset from the principal path. A folding mirror in the principal optical path, when in a stowed position, permits the first device to collect and focus the axial emission component onto the primary aperture. In an operative position, the mirror permits the second device to collect and focus the radial emission component onto the primary aperture. A system is provided for communicating the radial emission component to the folding mirror.

2 Claims, 3 Drawing Sheets

DUAL-AXIS PLASMA IMAGING SYSTEM FOR USE IN SPECTROSCOPIC ANALYSIS

BACKGROUND OF THE INVENTION

The present invention relates to atomic spectrometry and more particularly to apparatus for inductively coupled plasma spectrometry and the like.

In spectroscopic analysis of the alkali elements (sodium-Na, lithium-Li, potassium-K, cesium-Cs and rubidium-Rb), non-linearities are exhibited which can lead to significant inaccuracies in analysis. These non-linearities usually manifest themselves in two ways. First, the signals produced by each element in solution do not correlate linearly with increases in their concentration. Second, for a given concentration of an alkali element, e.g., Na, changes in the concentration of the other alkali elements, e.g., K, alter the Na signal. These non-linear effects (known as easily ionizable element or "EIE" effects) are believed due to the relatively low electron density of the plasma and the relatively cool temperature of both the preheating zone and the tail plume of the plasma.

In conventional plasma imaging systems for spectroscopic analysis, the plasma is viewed axially. Since the plasma axis is coincident with the optical viewing axis of the spectrometer, the entire plasma is observed. This includes the preheating zone and the tail plume where matrix interferences or EIE effects are pronounced. While conventional axial viewing systems have been noted for their detection limits, sensitivity, precision and reduced background signal interference, EIE effects persist leading to significant inaccuracies in spectroscopic analysis.

BRIEF STATEMENT OF THE INVENTION

It is therefore an object of the present invention to minimize easily ionizable element effects and consequential inaccuracies during plasma optical emission spectrometry of alkali elements.

Another object of the present invention is to provide an alternative view of a plasma's optical emission during spectrometry which excludes the preheating zone.

Still another object of the present invention is to provide a spectrometer with an alternative view of a plasma's optical emission which excludes the tail plume.

Yet another object of the present invention is to eliminate inaccuracies in the spectroscopic analysis of alkali and other elements.

A further object of the present invention is to minimize EIE effects without sacrificing the detection limits, sensitivity, precision or background reduction provided by conventional axial viewing apparatus.

Still another object of the present invention is to provide a durable, reliable, economical apparatus and method of plasma optical emission spectrometry.

The invention meets these objects by using a dual-axis plasma imaging system. A plasma discharge system, such as a plasma torch and induction coil, excites a flow of material to be analyzed, effecting a plasma optical emission therefrom. At least one spectrometer is used to analyze the emission. A first optical imaging device in a primary optical path collects and focuses an axial component of the emission onto a primary aperture of the spectrometer. A radial emission component is collected and focused onto the primary aperture by a second optical imaging device in a secondary optical path. A system communicates the radial emission component to the spectrometer, e.g., via a folding mirror.

In accordance with one aspect of the present invention is a dual-axis plasma viewing system for use in spectroscopic analysis of material, comprising:

a plasma discharge system for exciting a flow of material to be analyzed so as to effect plasma optical emission therefrom;

a spectrometer for analyzing the emission;

a dual-axis optical imaging system for collecting and focusing axial and radial emission components onto a primary aperture of the spectrometer; and a system for communicating the radial emission component to the spectrometer.

In accordance with another aspect of the present invention is a dual-axis plasma viewing system for use in spectroscopic analysis of material, comprising:

a plasma discharge system for exciting a flow of material to be analyzed so as to effect plasma optical emission therefrom;

first and second spectrometers for analyzing the emission; and a dual-axis optical imaging system for collecting and focusing an axial emission component onto a primary aperture of the first spectrometer, and a radial emission component onto a primary aperture of the second spectrometer.

In accordance with a further aspect of the present invention is a method of plasma optical emission spectrometry, which comprises the steps of:

receiving a flow of material to be analyzed in an upstream inlet end of a plasma torch tubular member;

actuating an induction coil of the member at its downstream discharge end so as to effect plasma optical emission from the material;

collecting a radial component of the emission using an optical imaging device in an optical path angularly offset from an optical path of an axial component of the emission; and communicating the radial emission component to the spectrometer.

The present invention will now be further described by reference to the following drawings which are not intended to limit the accompanying claims.

BRIEF DESCRIPTION OF THE DRAWINGS

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
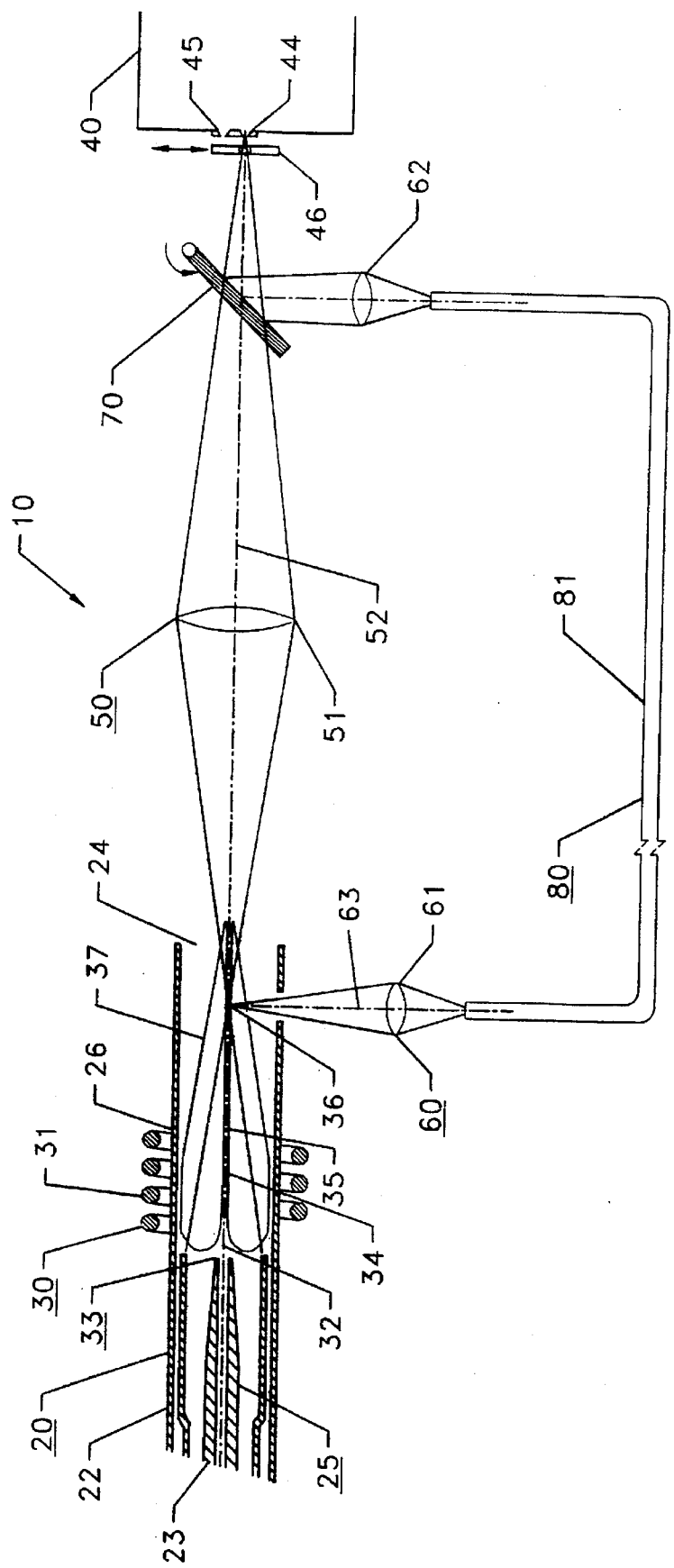
FIG. 1 is a schematic illustration of a dual-axis plasma imaging system for use in spectroscopic analysis, in accordance with one aspect of the present invention.

Referring now to the drawings and more particularly to FIG. 1, there is shown generally a dual-axis plasma imaging system 10 for use in spectroscopic analysis of material, according to one aspect of the present invention.

The system includes a plasma torch 20 for receiving a flow of material to be analyzed, such as an alkali element, and discharging the material. Plasma torch 20 is preferably a conventional inductively coupled plasma (or ICP) torch which comprises a tubular member or tube 22. An upstream inlet end 23 of the tube is configured for receiving the flow of material to be analyzed. A downstream end 24 is shaped appropriately for discharging the material. An induction coil 30 such as a conventional load coil 31 is located preferably toward downstream tube end 24 to effect a plasma optical emission from the material as it flows through the tube.

An injector tube 25 is positioned inside tube 22 between the upstream inlet end and that portion 26 of the tube surrounded by the induction coil. In operation, a sample aerosol and carrier gas flows into the injector tube through the upstream inlet end. The flow emerging from tube 25 is then activated by the load coil so as to produce the plasma optical emission.

This emission comprises a base region 32 of the plasma, known as the preheating zone (or PHZ), which forms in proximity to injector tube outlet 33. In this region, matrix or EIE effects are pronounced. Another portion of the emission is induction region 34. This region comprises a two part plume which forms within the induction coil portion of tube 22.

Typically at or near the downstream end of the induction coil is an initial radiation zone 35 (or IRZ) of the emission. A normal analytical zone 36 (or NAZ) usually forms above the downstream end of the coil, e.g., about 1 cm. Then, emerging from the downstream end of the tube is tail plume 37 where matrix or EIE effects are also pronounced.

It has been found that the EIE effects produced by the preheating zone and the tail plume are together responsible for a substantial portion of the inaccuracies produced during inductively coupled plasma spectrometry of alkali elements.

The present invention provides a first spectrometer 40 for analyzing the plasma optical emission. A first optical imaging device 50 collects and focuses the axial emission component onto the primary aperture of the first spectrometer. The device is positioned in a principal optical path 52, which is preferably between the plasma torch and the first spectrometer. A second optical imaging device 60 in a secondary optical path 63 collects and focuses a radial component of the emission, the secondary path preferably being angularly offset from the principal optical path.

A folding mirror 70 in the principal optical path, when in a stowed position, e.g., parallel to the principal path, permits the first optical imaging device to collect and focus the axial emission component onto the first spectrometer's primary aperture. In an operative position, such as the orientation in FIG. 1, the mirror permits the second device to collect and focus the radial emission component onto the primary aperture. The radial emission component is then communicated to the folding mirror by communication system 80.

The first optical imaging device, according to one aspect of the present invention, is a first lens 51 such as a conventional convex quartz or fused silica lens. This lens is located downstream of the tail plume to collect and focus the optical plasma emission onto the primary aperture. The first lens preferably lies within the principal optical path, defined between tube 22 and the first spectrometer, and shares a common central axis therewith.

Second optical imaging device 60 such as second lens 61, e.g., a conventional convex quartz or fused silica lens, is angularly offset from the principal path, in secondary optical path 63, to collect and focus the radial emission component.

In the present embodiment, the secondary path is offset from the principal path about 90 degrees. However, it is appreciated that other angles could be used, so long as the base region of the plasma and its tail plume are not imaged onto the primary aperture of the first spectrometer.

System 80, for communicating the radial emission component to folding mirror 70, is preferably a fiber optic system 81. This fiber optic system may comprise conventional fiber optics including one or more fiber optic strands and/or other characteristics and features of fiber optic technology. However, other suitable communication or transmission means may be utilized, giving consideration to the purpose for which the present invention is intended.

The communication system may also include a third optical imaging device or lens 62, as shown in FIG. 1. Lens 62, e.g., also a conventional convex quartz or fused silica lens, collects the radial emission component from the fiber optic system and focuses it upon folding mirror 70.

This lens and fiber optic system is desirably coupled to and angularly offset from principal optical path 52. Also, it is preferred that the principal path be coincident with the plasma torch axis of rotational symmetry.

By combining a lens/fiber optic system, in this fashion, with a folding mirror allows light from the plasma to be collected both radially and axially, and imaged onto the primary aperture of the first spectrometer. Hence, when analyzing elements that do not exhibit substantial matrix effects because of end-on viewing, the folding mirror is rotated out of the principal optical path and light is collected along the torch and principal optical axes. When elements are to be analyzed that do exhibit matrix effects, the mirror is rotated into the principal optical axis. This blocks light emitted axially along the plasma, and reflects light from the fiber optic system, that is viewed radially, onto the entrance aperture of the first spectrometer.

As a result, a single spectrometer views all wavelengths of the emission, whether emitted axially or radially of the torch axis. In addition, the EIE effects so pronounced with Group I or alkali elements are reduced dramatically. The spectrometer's view, whether of the axial or radial emission component, is as if it were observing them along the torch axis.

Figure 3:
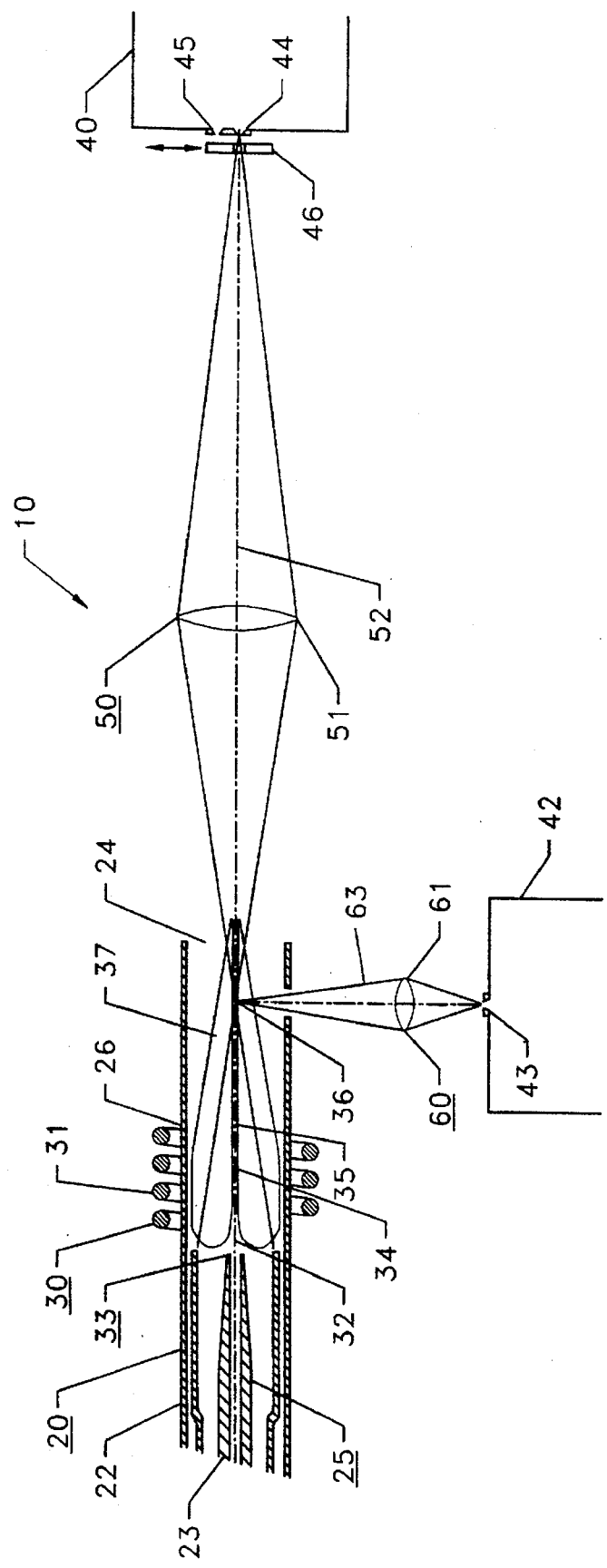
FIG. 3 is a schematic illustration of a dual-axis plasma imaging system for use in spectroscopic analysis, in accordance with a further aspect of the present invention.

In an alternative embodiment of the present invention, as shown in FIG. 3, the radial emission component is imaged onto primary aperture 43 of a second spectrometer 42. Initially, the first lens collects and focuses the axial component of the emission onto the primary aperture of first spectrometer 40. The first spectrometer then analyzes the axial component. The first lens is again desirably in the principal optical path between tube 22 and the first spectrometer.

Similarly, second lens 61 is preferably in the secondary optical path, angularly offset from the principal path, to collect the radial emission component and focus it onto the primary aperture of second spectrometer 42. Since the first spectrometer is generally dedicated to viewing the axial emission component, and the second spectrometer is usually committed to viewing the radial emission component, the folding mirror may be omitted from this embodiment.

While the present invention is shown and described using lenses as optical imaging devices, it is understood that any optical imaging means may be utilized, giving consideration to the purpose for which the present invention is intended. For instance, the transfer of radially emitted light (or a radial component of the plasma emission) may be accomplished using mirrors in place of the lenses, or in combination with lenses. A second, separate spectrometer is then employed to view the emission signals radially while the primary spectrometer views light which is emitted axially. A conventional mirror or prism, or a combination of mirrors and/or prisms, may also be suitable, alternatively or concurrently with the embodiments presented herein, within the spirit and scope of the present invention.

Appropriate spectrometers for use in the present invention include a sequential scanning monochromater, a Rowland circle polychromater, and/or an Echele spectrometer employing an array detector. The first and second spectrometers may be selected from one of the foregoing spectrometers or any combination thereof.

A spectrometer, according to a further embodiment, contains two entrance apertures: a primary aperture 44 for viewing the axial emission along the principal axis; and a secondary aperture 45 for viewing the radial emission along the secondary optical path.

Alternatively or concurrently therewith, as shown in FIG. 3, an aperture flag 46 (e.g., blockage, a shutter or the like) is placed between the entrance apertures of the spectrometer and the focused emission. The aperture flag is preferably a thin sheet of metal or the like. In a first flag position, the flag blocks the radial component of the emission while permitting the axial component to pass through the primary aperture of the spectrometer. In a second flag position, the flag blocks the axial emission component while permitting the radial component to pass through the secondary aperture of the spectrometer.

Figure 2:
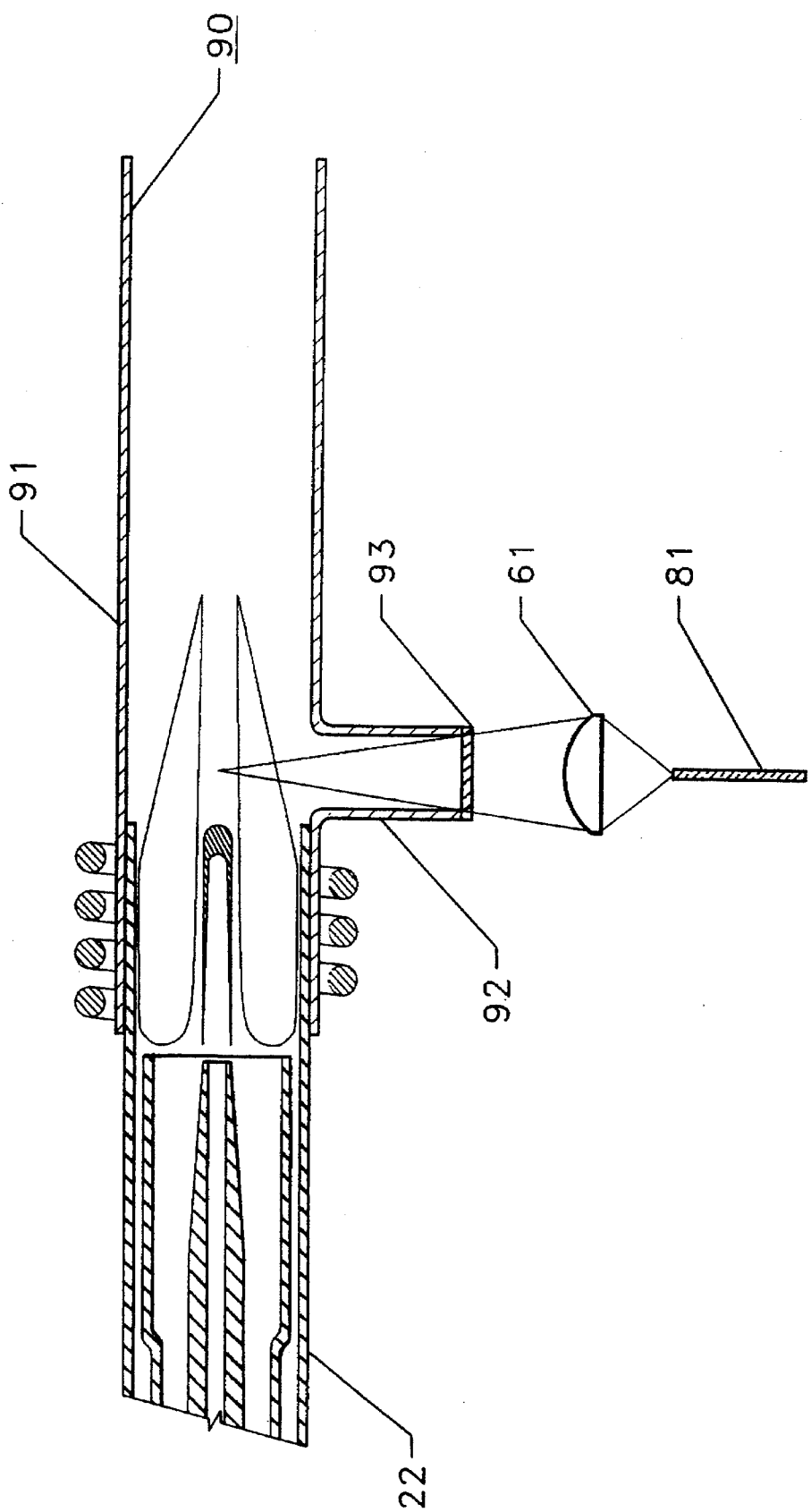
FIG. 2 is a schematic illustration of a dual-axis plasma imaging system for use in spectroscopic analysis, in accordance with another aspect of the present invention.

According to still another aspect of the present inventions, as shown in FIG. 2, a "T" tube 90 is provided adjacent the tail plume or discharge end of the tube. One purpose of the "T" configuration is to keep air away, providing a more stable plasma for analysis. The "T" tube comprises a main tube 91 connected to and coincident with the central axis of tube 22. A side arm 92 of the "T" is open to the atmosphere and oriented generally perpendicular to tube 22. According to another embodiment, the "T" is open to the atmosphere but purged with a flow of inert gas, e.g., argon, to stabilize the plume.

Optionally, a window 93, e.g., of quartz, is provided at one end 94 of the side arm for receiving and collecting the radially emitted light. The first lens is positioned, e.g., coincident with the side arm central axis, to collect the radial emission component and focus it into the fiber optic system.

In accordance with yet another aspect of the present invention is a method of plasma optical emission spectrometry. Initially, the flow of material to be analyzed is received in the upstream inlet end of the plasma torch tube. The induction coil of the tube is then actuated to effect plasma optical emission from the material. Next, the emission is collected using the first lens positioned in the principal optical path (coincident with the torch axis of rotational symmetry), and focused onto the primary aperture of the first spectrometer. Concurrently or subsequently, a radial component of the emission is collected using the second lens in the secondary optical path. (angularly offset from the principal path). The radial emission component is then communicated to the spectrometer.

A further embodiment is directed to a method of plasma optical emission spectrometry which comprises the steps of receiving a flow of material to be analyzed in the upstream inlet end of the plasma torch tube; actuating the induction coil of the tube so as to effect plasma optical emission from the material; collecting the emission using the first lens positioned in the principal optical path; focusing the emission onto the primary aperture of the first spectrometer; collecting a radial component of the emission using the second lens in the secondary optical path; and communicating the radial emission component to the primary aperture of the second spectrometer.

The communicating step preferably includes the collection of the radial emission component at a selected location past the end of the plasma torch tube, i.e., at a point outside the tube. Alternatively, the radial emission component is collected at a point inside the tube. Collection is aided by a hole placed in the side of the tube member which provides an unobstructed view of the emission region inside the tube.

It will be understood, however, by those skilled in the art that the foregoing method steps can be varied, giving consideration to feasibility and preference.

Overall, the present invention provides cost-effective means of spectroscopic analysis of inductively coupled plasma emission which minimizes matrix interferences or EIE effects without sacrificing the detection limits, sensitivity, precision or background reduction of conventional apparatus.

Although the present invention is shown and described in connection with Group I or alkali elements, it may be utilized for improving spectrometry of other materials, alternatively or concurrently therewith, giving consideration to purposes for which the present invention is intended. In addition, while the present invention has been illustrated as using a plasma torch and induction coil arrangement to excite a flow of material to be analyzed, it is appreciated that any plasma discharge system which effects plasma optical emission may be utilized, consistent with the spirit and scope of the present invention.

Various modifications and alterations to the present invention may be appreciated based on a review of this disclosure. These changes and additions are intended to be within the scope and spirit of this invention as defined by the following claims.

What is claimed:

1. A dual-axis plasma imaging system for use in spectroscopic analysis of material, comprising:

a plasma torch having a tubular member with an upstream inlet end for receiving a flow of material to be analyzed and a downstream end for discharge of the material;

an induction coil for effecting plasma optical emission from the material;

a spectrometer for analyzing the emission, the spectrometer having a primary aperture for viewing an axial emission component and a secondary aperture for viewing a radial emission component;

a first optical imaging device for collecting and focusing the axial emission component onto the primary aperture of the spectrometer, the first device being in a principal optical path between the tubular member and the spectrometer;

a second optical imaging device in a secondary optical path for collecting and focusing the radial emission component onto the secondary aperture of the spectrometer, the secondary path being angularly offset from the principal path;

a folding mirror in the principal optical path which, in a stowed position, permits the first device to collect and focus the axial emission component onto the primary aperture and, in an operative position, permits the second device to collect and focus the radial emission component onto the secondary aperture;

a system for communicating the radial emission component to the folding mirror, the communicating system including at least one fiber optic system and a third optical imaging device for collecting the radial emission component from the fiber optic system and focusing the same upon the folding mirror;

a flag between the primary and secondary apertures, and the focused emission which, in a first flag position, blocks the radial emission while permitting the axial emission component to pass through the primary aperture, and in a second flag position blocks the axial emission component while allowing the radial emission component to pass through the secondary aperture; and a generally "T" shaped member adjacent the discharge end of the tubular member, the "T" shaped member having a sidearm portion for collecting the radial emission component.

2. A dual-axis plasma imaging system for use in spectroscopic analysis of material, which comprises:

a plasma torch having a tubular member with an upstream inlet end for receiving a flow of material to be analyzed and a downstream end for discharge of the material;

an induction coil for effecting plasma optical emission from the material;

a spectrometer for analyzing an axial component of the emission, the spectrometer having a primary aperture for viewing an axial emission component and a secondary aperture for viewing a radial emission component;

a first optical imaging device in a principal optical path for collecting and focusing the axial emission component onto the primary aperture of the spectrometer, the principal path being defined between the tubular member and the spectrometer;

a second optical imaging device in a secondary optical path for collecting and focusing the radial component of the emission onto the secondary aperture of the spectrometer, the secondary path being angularly offset from the principal path;

a folding mirror in the principal path which, in a stowed position, permits the first device to collect and focus the axial emission component onto the principal aperture of the spectrometer and, in an operative position, permits the second device to collect and focus the radial emission component onto the secondary aperture, the second device collecting and focusing the radial emission component into a fiber optic system, the fiber optic system communicating the radial emission component to a third optical imaging device, the third device collecting and focusing the radial emission component onto the folding mirror;

a flag between the primary and secondary apertures, and the focused emission which, in a first flag position, blocks the radial emission while permitting the axial emission component to pass through the primary aperture, and in a second flag position blocks the axial emission component while allowing the radial emission component to pass through the secondary aperture; and a generally "T" shaped member adjacent the discharge end of the tubular member, the "T" shaped member having a sidearm portion for collecting the radial emission component.

* * * * *